United States Patent
Gebran

[11] Patent Number: 5,827,170
[45] Date of Patent: Oct. 27, 1998

[54] THERAPEUTIC MAGNETIC VORTEX ORNAMENT AND DEVICE

[76] Inventor: Emile Gebran, 108-22 Queens Blvd., Forest Hills, N.Y. 11375

[21] Appl. No.: 774,145

[22] Filed: Dec. 26, 1996

[51] Int. Cl.$^6$ ........................................... A61N 1/00
[52] U.S. Cl. ................................................... 600/15
[58] Field of Search ............................... 600/9–15

[56] References Cited

U.S. PATENT DOCUMENTS

| | | | |
|---|---|---|---|
| 237,939 | 2/1881 | Wilson . | |
| D. 245,769 | 9/1977 | Chihara | D11/13 |
| D. 249,780 | 10/1978 | Gonzalez | D11/30 |
| D. 253,049 | 10/1979 | Escher | D11/34 |
| D. 329,991 | 10/1992 | Gonzalez | D11/30 |
| D. 367,384 | 2/1996 | DiFranco et al. | D6/474 |
| 2,637,887 | 5/1953 | Goodman et al. | 24/230 |
| 3,509,734 | 5/1970 | Lederer | 63/15 |
| 3,835,664 | 9/1974 | Nesbit | 63/15.6 |
| 3,885,383 | 5/1975 | Tanaka | 63/4 |
| 3,921,620 | 11/1975 | Nakayama | 128/1.3 |
| 3,943,912 | 3/1976 | Nakayama | 128/1.3 |
| 4,095,587 | 6/1978 | Ishikawa | 128/1.3 |
| 4,162,672 | 7/1979 | Yazaki | 128/1.3 |
| 4,480,596 | 11/1984 | Shumiyashu | 128/1.3 |
| 4,905,335 | 3/1990 | Tervola | 7/169 |
| 5,017,185 | 5/1991 | Baermann | 600/15 |
| 5,035,017 | 7/1991 | Komuro | 600/9 |
| 5,036,681 | 8/1991 | Schaerer | 63/14.5 |
| 5,038,779 | 8/1991 | Barry et al. | 128/402 |
| 5,050,276 | 9/1991 | Pemberton | 24/303 |
| 5,092,835 | 3/1992 | Schurig et al. | 600/9 |
| 5,116,304 | 5/1992 | Cadwell | 600/13 |
| 5,135,507 | 8/1992 | Park | 600/13 |
| 5,197,168 | 3/1993 | Levy | 24/303 |
| 5,226,020 | 7/1993 | Li | 368/10 |
| 5,333,767 | 8/1994 | Anderson | 224/183 |
| 5,387,176 | 2/1995 | Markoll | 600/14 |
| 5,432,986 | 7/1995 | Sexton | 24/303 |
| 5,453,073 | 9/1995 | Markoll | 600/14 |
| 5,453,074 | 9/1995 | Imoto | 600/15 |
| 5,518,495 | 5/1996 | Kolt | 600/13 |
| 5,538,495 | 7/1996 | Ardizzone | 600/9 |

*Primary Examiner*—John P. Lacyk
*Attorney, Agent, or Firm*—Steinberg & Raskin, P.C.

[57] ABSTRACT

A magnetic vortex device in which a dia-magnetic square pyramid is placed in a uniform magnetic field generated between exposed end regions of a C or U-shaped magnet having opposed polarity. In the magnetic field, lines of magnetic flux extend uniformly between the North and South poles defined at the end regions. A support plate is attached at both end regions and holds a pyramid in the middle of the magnetic field, so that two opposing flanks of the pyramid face the North and South poles of the magnet, thus causing the magnetic flux to avoid the dia-magnetic pyramid and forming a varying distribution of lines of force around it in the shape and characteristics of approximately a double semi-vortex.

20 Claims, 5 Drawing Sheets

THERAPEUTIC MAGNETIC VORTEX ORNAMENT AND DEVICE

REFERENCE TO RELATED DOCUMENT

Reference is made to Disclosure Document Number 380360 filed Jul. 31, 1995 by the present applicant.

FIELD OF THE INVENTION

The present invention relates in general to an object for providing a therapeutic effect based on magnetism and more specifically to an article of jewelry in which a magnetic field is generated between spaced-apart North and South poles and an interceptor structure, such as a square dia-magnetic pyramid, is placed within the magnetic field to cause a change in the magnetic flux lines constituting the magnetic field and thereby provide enhanced therapeutic effects when worn by a person or situated proximate a portion of the body. More particularly, the present invention relates to the creation of a magnetic vortex formed when a dia-magnetic pyramid having a square base is placed in a magnetic field, thereby simulating the salutary environmental natural magnetic condition prevailing in the vicinity around the most famous pyramid in the world, the Cheops pyramid in Egypt.

BACKGROUND OF THE INVENTION

Pyramids are important landmarks. They themselves and the area in their vicinity are considered by many to be healing centers of the earth. The Cheops pyramid in Egypt, also known as the Great Pyramid, is one such example. It has been said that the infant mortality rate in the area surrounding the Cheops pyramid is negligible, if not totally absent. Although most of the research on the healing or phenomenal powers of pyramids have focused on the energies manifested in their interiors, the health and other benefits reported by those living around pyramids suggests that the power of the pyramid is not only derived from within it but from around it as well. The magnetic line of force or tube of magnetic flux is in reality a spherical wave of infinitesimally small amplitude and wavelength related to and produced by a moving and rotating electron. It is not stationary but dynamic. A wave can be generated, increased or decreased and can even be made to vanish. A vortex produced by magnetic lines of force is therefore relatively dynamic and more effective for certain purposes than a uniform magnetic field which can be considered as static comparatively to a magnetic vortex where the horizontal magnetic intensity or the crowding of lines of force, varies from a maximum at the base to a minimum at the apex. However, the vortical energy at the apex is huge as will be evident from the fact that it is where the upwardly magnetic flux tend to move due to the upward inclination of the sides of the pyramid.

To be more specific, magnetic energy can be imparted to non-magnetic materials and stored in them for immediate or future use. The following illustration will serve as an example. Water will be chosen, since it is not properly magnetic and because it is universally recognized as a carrier of life for all living beings. Although not a magnetic material, water has been charged with magnetic energy. This energy has been detected by nuclear magnetic resonance techniques and by chemical analysis, and it has been found to be retained in water for a specific amount of time according to the charging process.

This magnetic energy which in water affects the hydrogen bond, as evidenced by the two methods previously mentioned, may as well be imparted to and stored in any medicine, drug and food, and above all be applied directly to the human body which, it is well known, is composed of about 75% water.

There has long been a keen interest in the healing of diseases and cases caused by lack of living in harmony with earth, for example rheumatism, arthritis and similar related ailments, by devices utilizing magnets placed on, positioned in proximity to or moved over the ailing body parts. For example, it is commonly known that magnetic fields of flexible magnetic foils can stimulate blood circulation and that the healing process in the case of bone fractures is accelerated when an electromagnetically produced alternate field of varying frequency and/or strength is allowed to act on the point of fracture. Such uses of magnetic energy have been well documented, and include magnetized bracelets and other articles of jewelry as well as magnetized articles of clothing and machines which subject the body to static or fluctuating magnetic fields. Examples of such therapeutic devices and articles of clothing include those described in U.S. Pat. Nos. 237,939 (Wilson)—a wearable vest for imparting the therapeutic influence of magnetism to the human body, 3,943,912 (Nakayama)—a belly-band with magnetic treatment means, 4,162,672 (Yazaki)—an adherent magnetic sheet for application to the human body, e.g., to cure stiffness in the shoulder and pains in the waist and muscles with its magnetic effects, 4,480,596 (Shumiyashu)—a belt with magnets, 5,017,185 (Baermann)—a wrap including magnets, 5,035,017 (Komuro)—a magnetic sleeping mat, 5,038,779 (Barry et al.)—a vest having a pouch for receiving a heated object (non-magnetic but practical for a magnetic object), 5,092,835 (Schurig et al.)—an apparatus in which a constant magnetic field is applied in a cap or strap arrangement to the head or nervous system of a person, 5,116,304 (Cadwell)—a magnetic stimulator with skullcap-shaped coil, 5,387,176 (Markoll)—a machine for treating organs by applying a magnetic field by means of an annular coil, 5,453,073, (Markoll)—a machine for treating organs by applying a magnetic field by means of an annular coil, 5,453,074 (Imoto)—an electromagnetic therapy machine, 5,518,495 (Kolt)—an arthritis treatment machine including a wire-wound bobbin for generating a magnetic field, and 5,538,495 (Ardizzone)—a magnetic pad with alternating polarized zones.

Magnetic articles of jewelry may generally be divided into two groups. The first group includes devices which utilize the power of magnetism for its holding or attractive power, i.e., to fasten a multi-piece of jewelry together or to attract and pick up small loose metal objects. Examples of such items include those described in U.S. Pat. Nos. 2,637,887 (Goodman et al.)—a magnetic jewelry clamp, 3,509,734 (Lederer)—a ring with a magnetically biased ornamental signet member, 3,835,664 (Nesbit)—a ring with a magnetically secured setting, 3,885,383 (Tanaka)—an expandable band with magnetic contracting system, 4,905,335 (Tervola)—a ring having an exposed magnet for attracting or holding loose objects, 5,036,681 (Schaerer)—an earring attached through magnetic attraction of two elements thereof to the ear, 5,050,276 (Pemberton)—a magnetic necklace clamp, 5,197,168 (Levy)—a magnetic closure for jewelry, 5,333,767 (Anderson)—a wrist mounted magnetic holder and 5,432,986 (Sexton)—a magnetic fastener for jewelry and belts.

The second group of magnetic articles of jewelry or other accessories belongs to those which use or appear to use the power of magnetism for healing and therapeutic purposes. Examples of such articles of jeweley and accessories include those described in U.S. Pat. Nos. Des. 245,769 (Chihara)—a magnetic medical necklace, 3,921,620 (Nakayama)—a wrist band with permanent magnets, 4,095,587 (Ishikawa)—a magnetic belt, chain, bracelet or necklace, 5,137,507 (Park)—a magnetic ring for stimulating fingers or toes, and 5,226,020 (Zhi Li et al.)—a wrist watch with a magnetic body.

In the prior art relating to pyramids, reference is made to U.S. Pat. Nos. Des. 249,780 (Gonzalez), Des. 253,049 (Escher), Des. 329,991 (Gonzalez), Des. 367,384 (DiFranco et al.). All of the uses of the pyramids described in these patents are for mere ornamental purposes only associated with different jewelry applications, e.g., the Gonzalez patents which disclose substantially circular rings with a decorative pyramid.

As discussed in detail below, the present invention differs from all of these mere ornamental prior art devices and articles of jewelry in that it combines the established healing power of magnetism and the novel effect of a disturbance in the magnetic field created by the placement of a three-dimensional structure such as a pyramid, in a definite, logical, scientific, practical and efficient way to easily produce, without moving parts, a vortical magnetic field having a whirlpool movement which may penetrate more gently in the body and produce a more soothing, continuous and appropriate effect than that produced by a magnet moved by hand or by other means. One particularly significant advantage of this is that while one cannot live continuously under a healing machine, a person can wear indefinitely a small pyramidal magnetic vortex article as an amulet or a piece of jewelry in accordance with the invention as disclosed herein.

OBJECTS AND SUMMARY OF THE INVENTION

Accordingly, it is an object of this invention to provide a new vortical magnetic device for creating a whirlpool of magnetic energy to be used for therapeutic and/or healing purposes.

It is another object of this invention to provide a therapeutic and pleasant magnetic vortex device to continuously secure and store a useful reserve of magnetic energy in the body.

More particularly, it is an object of this invention to provide a magnetic vortex device which is designed to simulate the salutary condition of environmental natural magnetism surrounding the most famous pyramid in the world, the Great Pyramid of Cheops in Egypt, by positioning a dia-magnetic square pyramid between a North and South pole magnetic field thereby diverging the otherwise uniform magnetic field by intercepting the magnetic flux lines defining the magnetic field. In other words, the magnetic flux lines are usually direct lines between the poles but when a pyramid of a dia-magnetic material, i.e., a material which is not magnetized or magnetizable, is interposed between the poles, it intercepts the magnetic flux lines, blocking the direct route between the poles so to speak, and causes them to follow an indirect path between the poles.

Another object of this invention is to provide a magnetic vortex device which is beautiful and ornamental for both men and women, which has specific healing magnetic effects in a pleasant way, without the boredom of subjecting patients to healing machines or bulky magnetic wear.

It is still another object of this invention to provide a magnetic vortex device which is suitable for surrounding the neck, eyes, ears, elbows, wrists, fingers, knees, ankles and other important parts of the body to which therapy via magnetism is desired.

In order to achieve these objects and others, in accordance with the invention, a magnetic vortex simulating device for applying a magnetic field to the human body in order to treat ailments and/or diseases such as, for example, rheumatism, arthritis, bone fractures and muscle stiffness as well as to stimulate blood circulation includes a frame, means arranged in connection with the frame for generating a magnetic field defined by magnetic flux lines and means for intercepting the magnetic flux lines such as a dia-magnetic square pyramid supported in a position within the magnetic field by appropriate support means. In a most basic embodiment, the device includes a C-shaped or U-shaped permanent magnet having opposite end regions facing each other and constituting magnetic poles of opposite polarity, i.e., one North and the other South, to thereby produce a magnetic field defined by lines of magnetic flux extending otherwise uniformly between the two poles. The magnet has an approximate rectangular cross-section or a segment of a circle of a C-shape, and has its poles facing each other. The support means comprise a flat non-magnetic plate which connects the two opposed end regions of the magnet which constitute the poles and serves to position a dia-magnetic square pyramid, cone, sphere or other structure with a uniformly, varying shape, in the gap between the two poles.

In one preferred embodiment of this invention, the magnet comprises a C-shaped permanent magnet of small portable dimensions having oppositely facing North and South poles for producing a magnetic field extending between them. In the approximate middle of the gap between the two poles, a dia-magnetic square pyramid having a correspondingly small size is placed where the ratio of its height to the length of each side of its base is about 7:11, duplicating the height-to-base ratio of the Great Pyramid in Egypt.

In another embodiment of this invention, more than one pyramid can be seated on a supporting non-magnetic plate connecting the two opposed regions of the magnet and be positioned, so that each of the pyramids intercepts the magnetic field created between the spaced apart poles.

In still another embodiment of this invention, one pyramid is placed on one side of the supporting plate connecting the poles, i.e., between the poles in the magnetic field, and a second pyramid is placed on the other side of this plate, also within the magnetic field.

In yet another embodiment of this invention, the pyramid can be situated between the North and South poles of two separate magnets, provided the two other external South and North poles not facing the pyramids are preferably connected by a magnetic material, or otherwise magnetically coupled to one another, so as to produce a closed magnetic path or circuit through the frame.

Generally then, the magnetic vortex device for generating a magnetic vortex in accordance with the invention comprises a frame, magnetic field generating means arranged on the frame for generating a magnetic field, the generating means comprising at least one magnetized or magnetizable member arranged to have first and second opposed portions separated from one another to define a space therebetween and which are polarized or polarizeable such that the first portion has an opposite polarity than the second portion and magnetic flux lines extend between the first and second portions to generate the magnetic field, interceptor means for intercepting at least a portion of the magnetic flux lines extending between the first and second portions and preventing the portion of the magnetic flux lines from passing in a direct line between the first and second portions, and support means for supporting the interceptor means in a position between the first and second portions. The prevention of the magnetic flux from passing in a direct line through the interceptor means may be accomplished by making the interceptor means from a solid three-dimensional structure made of a dia-magnetic material, or any other material which is non-magnetizable and thus serves to divert the magnetic flux. In certain embodiments, the at least one member comprises a single C-shaped member constituting a permanent or flexible magnet and the frame is constituted by the C-shaped member. Alternatively, the generating means comprise an electromagnet coupled to the first and second portions of the at least one member.

The above, and other objects, features and advantages of the invention will be more fully apparent in the following detailed description of illustrative embodiments of the invention which is to be read in conjunction with the accompanying drawings.

BRIEF DESCRIPTION OF THE DRAWINGS

The invention will be readily understood by reference to the following detailed description when considered in connection with the accompanying drawings in which.

DETAILED DESCRIPTION OF THE PREFERRED EMBODIMENTS

Referring to the accompanying drawings wherein like reference numerals refer to the same or similar elements, in general, the magnetic vortex device in accordance with the invention includes a frame, magnets (or any magnetizable member) arranged in connection with the frame for generating a magnetic field in a space between, the magnets, a magnetic flux line interceptor member such as a pyramid which intercepts at least a portion of the magnetic flux lines extending between the magnets and prevents that portion from passing in a direct line between the magnets (which they would otherwise do in the absence of such an interceptor member), and a support structure for supporting the interceptor member in the space between the magnets. The frame is designed to be worn by a person, and can take the form of a ring, bracelet, necklace, ankle bracelet, or can be affixed to a structure worn by the person, such as eyeglasses or a clip so that a magnetic field is applied to a certain area of the body in order to treat an ailment or a disease such as, for example, rheumatism, arthritis, bone fractures and muscle stiffness as well as to stimulate blood circulation. The specific illustrated embodiments are discussed individually below.

Figure 1:
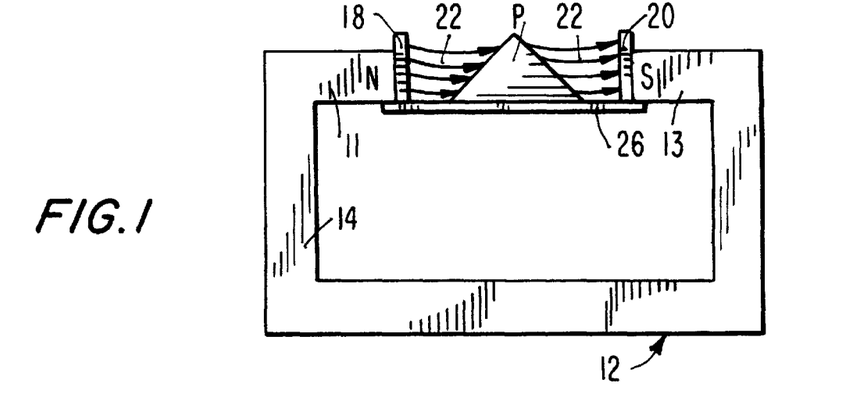
FIG. 1 is a side view of one embodiment of a magnetic vortex device according to the invention.
Figure 2:
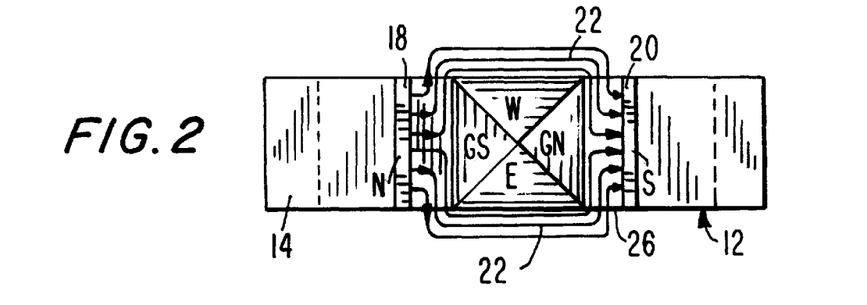
FIG. 2 is a top view of the magnetic vortex device shown in FIG. 1.

FIGS. 1 and 2 show a first, schematic embodiment of a magnetic vortex device in accordance with the invention which is generally denoted as 10. In this embodiment, the frame is constituted by a permanent magnet 12 having an approximate C-shape configuration and at least a portion 14 of which has a rectangular cross-section (as shown more clearly in FIG. 1). The magnet 12 includes two sections 11,13 facing one another, the gap therebetween being the opening of the C-configuration of the magnet 12. Two end pieces 18 and 20 are connected to the sections 11,13, respectively, which effectively constitute North and South poles respectively from where the densest part of the flux of the magnet takes place. The end piece 18 is polarized to have its North pole facing the gap between the end pieces 18,20 whereas the end piece 20 is polarized to have its South pole facing the gap between the end pieces 18,20.

Figure 7:
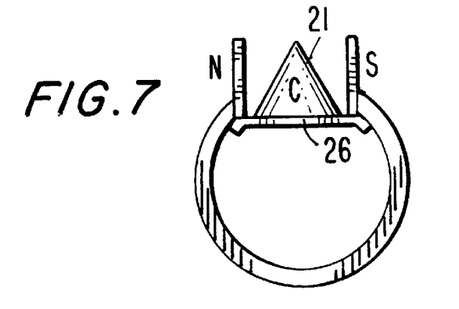
FIG. 7 is a schematic elevation of another modification of the device of FIG. 1, with the pyramid being replaced by a cone.
Figure 9:
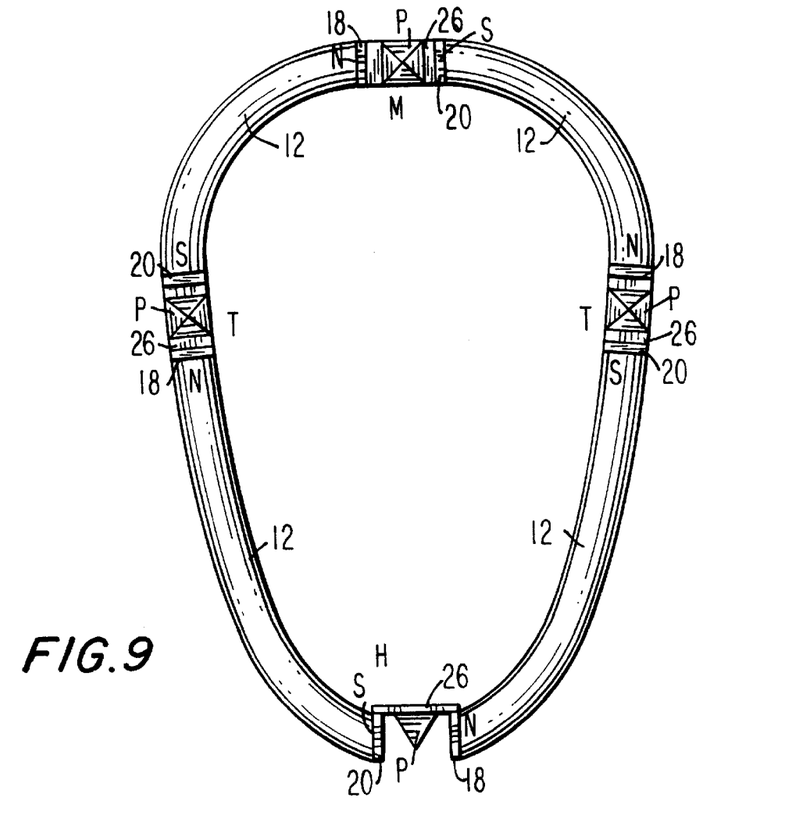
FIG. 9 is a plan view of a further embodiment showing four magnetic vortices of the device according to the invention.

It is to be noted however, that although the magnet 12 has been shown having a portion with a rectangular cross-section, portion 14, and C-shape or U-shape configuration (FIG. 1), any suitable shape and cross-section can be utilized with this invention without deviating from the scope and spirit thereof. For example, magnet 14 may be an electromagnet, a rigid permanent magnet or a flexible permanent magnet having a circular or semi-circular cross-section like a finger ring. Also magnet 14 may have a segment of a circle as shown in FIG. 7, or may entirely have a circular cross-section as shown in FIG. 9. In this latter embodiment, as well as in some others, a plurality of magnets 12 may be placed longitudinally one after the other, or in series as far as the flow of magnetic flux is concerned. Suitable permanent magnet materials in powder form are particularly: isotropic or anisotropic ferrites on a barium and/or strontium ferrite base, also lead ferrite or cobalt rare earth alloys and neodyme iron. The latter exhibit a particularly high energy product with high coercive force and residual magnetization.

Referring again to FIG. 1, the device 10 includes interceptor means, such as a pyramid P, for intercepting the magnetic field extending between the opposed poles of opposite polarity, i.e., between the end pieces 18,20 connected to magnet 12. Pyramid P is constructed of a non-magnetic or dia-magnetic material, which is a material which obstructs the flow of magnetic flux lines, so that in this case, the direct passage or flow of magnetic flux lines between the end pieces 18,20 is prevented. Mounting means such as a holding plate 26 extend between and couple the end pieces 18,20 connected to magnet 12 together, and also serves to support the pyramid P between the end pieces 18,20 connected to magnet 12. The holding plate or strap 26 or other mounting means are made of non-magnetic material and should attach the end pieces 18,20 connected to magnet 12 together mechanically, so as to form a collar, pendant or a bracelet which one can wear around the neck the arm or the ankle or other appendage. The end pieces 18 and 20, serving as the North and South poles respectively, connected to the magnet 12 are properly aligned so that the magnetic flux flows in the same direction and in series through the magnet 12, for example in a clockwise direction. In the above-described embodiments of the invention, a magnetic field is created by a magnet 12 and is defined by lines or tubes of magnetic flux 22, extending between the North and South poles always in the same direction and in a closed circuit or path.

Although the embodiment shown in FIG. 1 includes a single magnet 12 having a C-shape and portions 11,13 facing one another, it is possible to construct the device to include two magnets, each providing one portion which faces an opposed portion of the other magnet of opposite polarity, i.e., the North pole of one magnet faces the South pole of the other magnet, the members defining the North and South poles being coupled together by the mounting means such that the pyramid is situated therebetween within the flux lines. The other poles of the magnets may be coupled together through any magnetizable material in order that the magnetic flux through the device is in the same direction.

As shown in FIG. 1, the device 10 is constructed so that the magnet 12 has a flat lower surface, i.e., the middle region of the "C-shape", which enables it to be placed on a flat surface such as a table or in a box near or under the object or person to be affected by the magnetic vortex, i.e., for whom the therapeutic nature of the device is required. The holding plate 26 attached to the two ends of magnet 12 serves to support the interceptor means, in this case the pyramid P, preferably in or proximate the middle of the magnetic field created by the North and South poles formed by end pieces 18 and 20. End pieces 18, 20 as shown are metallic or magnetizable members fixedly attached to the ends of the magnet 12. However, the end pieces 18,20 can be removed altogether and the ends of the magnets thereby coupled by the holding plate 26. Other means for generating a magnetic field through an open space can also be applied in the invention without deviating from the scope and spirit thereof. It is also noted that the end pieces 18,20 are somewhat larger than the ends of the magnet 12. This will serve to enable an increase in the size of the magnetic field created between end pieces 18,20 without imposing a design requirements on the magnet 12.

With respect to the physical size of the device 10, the pole pieces 18 and 20 are dimensioned to have a height substantially equal to the height of the pyramid, or other interceptor means placed between the pole pieces 18,20, as well as a width substantially equal to the width of the base of the pyramid.

Referring now to FIG. 2, which is a top view of the device shown in FIG. 1, the lines of force or magnetic flux between the polarized end pieces 18,20 are represented by reference numeral 22. It has been recognized that the lines of magnetic force do not pass through the non-magnetic or dia-magnetic pyramid P, i.e., the magnetic field is intercepted since the forces lines avoid the pyramid face GS, geographic south, which is in direct opposition to the polarized North pole end piece 18, but rather divide sideways into two paths, one passing about the West side of the pyramid and the other passing about the East side of the pyramid. Further, the lines of force appear to bend upwards as shown in FIG. 1. It is a thus double deviation horizontally and vertically, shown in FIG. 14C giving the lines of force emanating from the polarized North end piece 18 a helical shape one twist around each of the East and West sides of the pyramid.

It should be mentioned here for the sake of exactness that in Cheops Pyramid, the four sides of the base are not equal, nor are they aligned exactly to the earth's magnetic North/South axis. The proportion of the height of the Cheops pyramid to the side of its square base is about 7:11, and thus the preferred dimensions of the pyramid P are the same thereas. A non-precise alignment of the pyramid with respect to the end pieces 18,20 connected to magnet 12 may provide additional therapeutic effects.

With respect to the nature of the magnetic field interception by the pyramid, the above-described embodiment, as well as the other embodiments of the invention described below, are for the most part designed to simulate the salutary environmental natural magnetic condition surrounding the Cheops pyramid in Egypt. It is a well known fact that the magnetic lines of force prefer to pass through a magnetic material rather than through a dia-magnetic material or a non-magnetizable material. When the lines of force encounter a magnetic material of high permeability, they converge towards it, but when a dia-magnetic material, such as a stone pyramid is placed in their way, they diverge and go around to avoid it and by doing so, the lines of force become crowded and denser at the base all around the sides of the pyramid. Therefore, when the device of the present invention is worn on the human body, the creation of the magnetic vortex from this point of increase of the density of magnetic flux provides penetration of the vortical energy in the part of the body on which the device is worn. To illustrate more graphically this point of increase of the density of magnetic flux, which lies as a basic foundation to the formation of a magnetic vortex as used in conjunction with this invention, reference is made to FIGS. 14–14C.

For the purpose of this illustration only, let us assume the pyramid to have a base of 10 meters at ground level and that one tube of force flows through each meter. Also, it is assumed that the pyramid is made of an absolutely dia-magnetic material, in other words no magnetic tubes of force at all pass through it. Now with these assumptions and considering the flux at ground level to be h, it is seen in FIG. 14 that the 10 tubes of force diverge and divide into two paths, each path consisting of 5 tubes, to pass around the pyramid adding themselves to the already existing tubes of force on the East and West sides of the pyramid, which are not shown for clarity.

Figure 14:
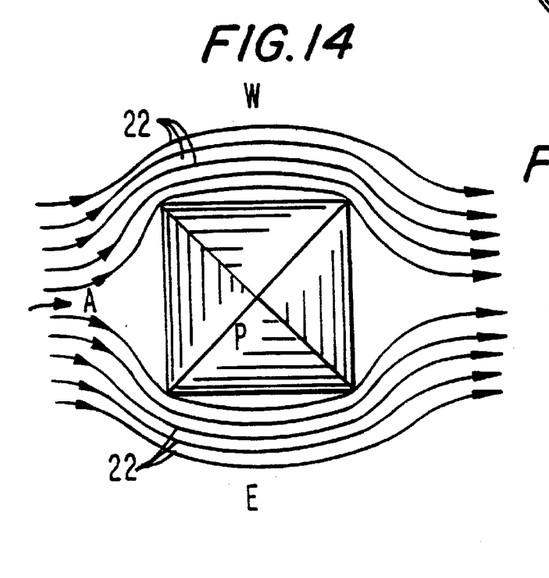
FIG. 14 is a top plan view showing the distribution of lines of force at ground level according to the invention.
Figure 14A:
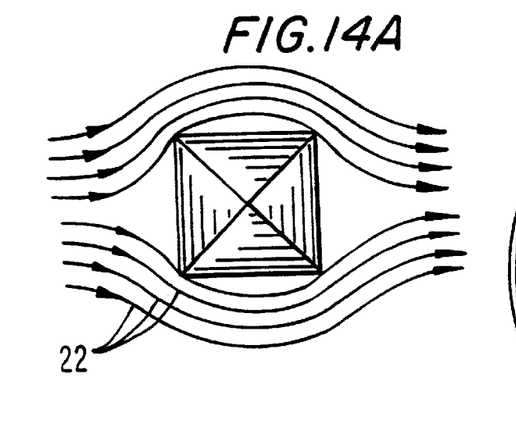
FIG. 14A is a top plan view showing the distribution of lines of force at a higher level above ground.
Figure 14B:
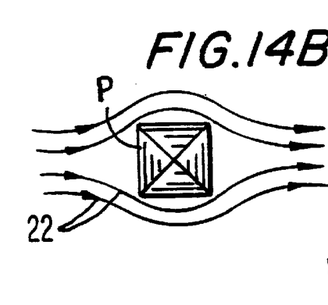
FIG. 14B is a top plan view showing the distribution of lines of force at a still higher level than that of FIGS. 14 and 14A.
Figure 14C:
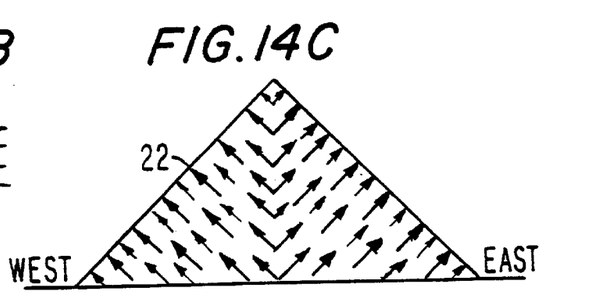
FIG. 14C is an elevational view showing the movement at different levels above ground of the lines of force toward the apex along arrow A of FIG. 14.

In this situation, at ground level we then have near and around the sides of the pyramid a crowding and an increase of tubes of force proportional to half the length of the base (FIG. 14). Referring now to FIG. 14A, there is shown a top view of the increase of tubes of force to the already existing tubes of force at a higher level, where the width of the pyramid is only about, e.g., 8 meters, instead of 10 meters. The increase to the already existing tubes of force at that level is only 4 tubes of flux or a number proportional to half the 8 meter width. Also in the distribution at still a higher level where the width of the pyramid is, e.g., 4 meters, the increase in the magnetic flux to the already existing flux is 2 tubes as shown in FIG. 14B. Thus, it can be seen that an increase in magnetic flux around a pyramid decreases with an increase in the height.

Figure 15:
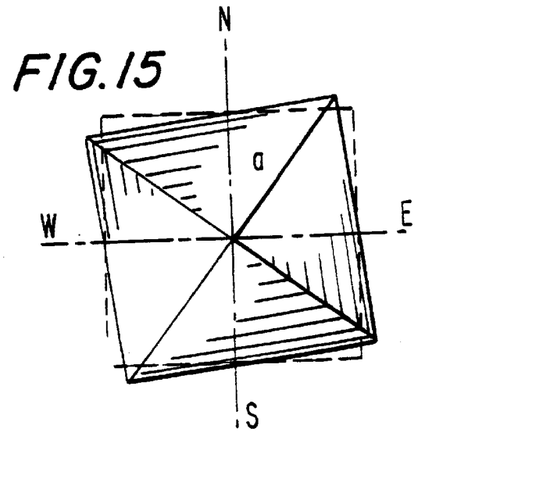
FIG. 15 is a plan view showing the inequality of the four sides of the pyramid which helps to accentuate the anti-clockwise shift of the magnetic vortex due to the alignment of the pyramid slightly out of the exact North/South axis of the earth.

It is moreover to be considered that the sides of the pyramid in this invention may not all be equal nor aligned exactly to the magnetic axis of magnet 12 as shown in FIG. 15, alignment with the magnetic axis of the magnet 12 being shown by the dotted lines and the actual embodiments being shown in solid lines. The object of this configuration, offset from the exact magnetic axis, is to produce, in the magnetic side twist, a semi-vortical whirlpool, one semi-vortex not in phase with the other or leading it in position. This has for effect, an easier penetration of the vortical magnetic energy in the part of the human being, thereby assuring a more lenient and comfortable assimilation respectively.

A mechanical analogy which sheds more light on the ease which takes place in the case of applying such a double of slightly unequal semi-vortices could be had from an ordinary wood screw which has along its shank two helicoidal threads running parallel, normally 180 degrees apart. When driven in the wood the two threads attack the wood at the same time thus meeting a double resistance. Whereas if the distances between the two threads were, for example, 179 degrees and 181 degrees, or one thread were shorter, it is obvious that the first attack in the wood is made easier and penetration effort less difficult to the driver, because only one thread enters at a time.

As an aside, it is the applicant's feeling that life seems to start in a vortical shape, one example is the snail. Another, is the well-known fact that DNA, the essential constituents of living matter found in the plasma of our blood, twist in a double helical or vortical shape in their behavior and reactions. Accordingly, magnetic energy, when prepared in a vortical shape as in this invention, will definitely reach being in harmony with, and affect beneficially the building stones of life, i.e., DNA which are themselves vortical energies.

Figure 2A:
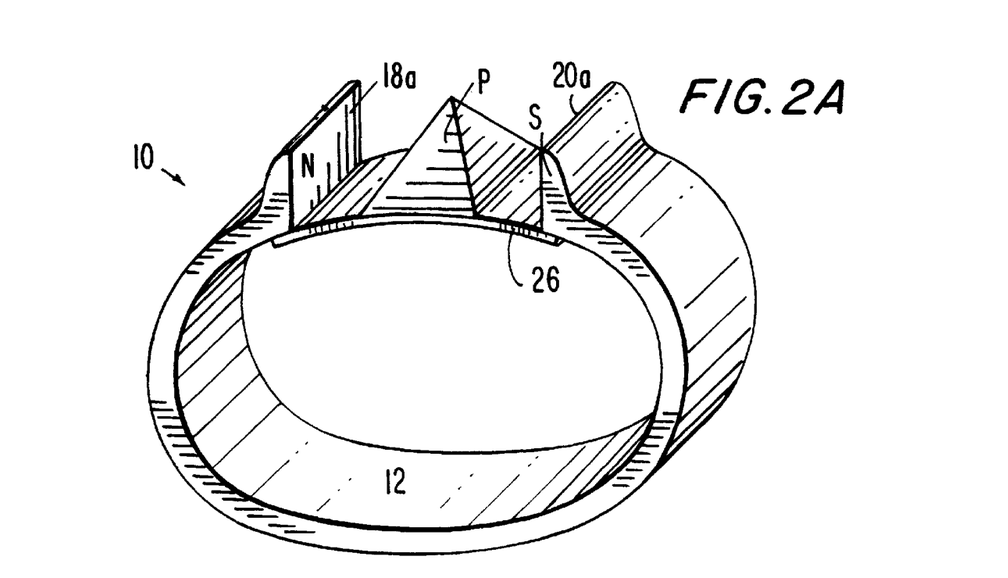
FIG. 2A is a perspective view of another embodiment of the magnetic vortex device according to the invention.

Referring now to FIG. 2A, which shows an embodiment of a magnetic vortex device in accordance with the invention in which the device 10 includes a substantially circular magnet 12, i.e., the frame is a ring and constitutes the magnet 12, which has a cut away portion whereby the edges of the magnet 12 at the cut away portion constitutes a North pole end portion 18a and a South pole end portion 20a (separate end pieces are not used in this embodiment as in FIGS. 1 and 2). A flat, slightly curved mounting plate is connected by suitable connecting means (not shown) to both edges of the magnet 12 at the cut away portion to connect the same and maintain the device in a substantially circular shape. A pyramid P is affixed to the mounting plate 26 at or in the vicinity of the middle of the space defined between the North pole end portion 18a and the South pole end portion 20a. This embodiment is most suitable for use as an ornament for digits of the body, i.e., the fingers or toes. Moreover, the end portions 18a,20a can be formed integral with the magnet 12.

Figure 3:
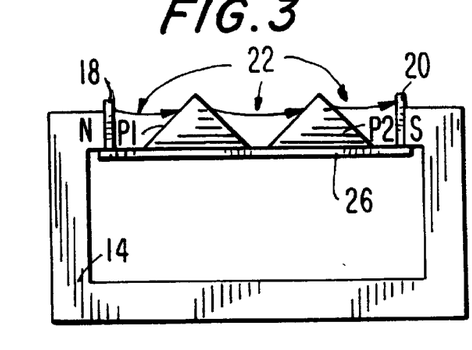
FIG. 3 is a schematic elevation view of an embodiment showing two magnetic vortices of the device according to the invention.
Figure 4:
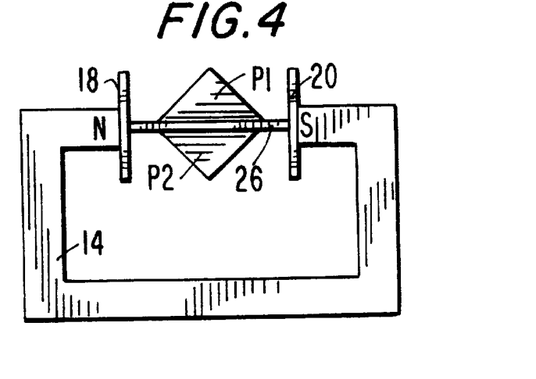
FIG. 4 is a schematic elevation view of still another embodiment of a magnetic vortex device according to the invention.

FIGS. 3 and 4 show alternative constructions of the interceptor means situated between the end pieces 18,20 attached to the exposed ends of the magnet 12 or between the exposed ends of the magnet 12 in the absence of such end pieces. In the embodiment shown in FIG. 3, the interceptor means comprises a pair of pyramids P1,P2 in series, both of which are mounted on the holding plate 26. In the embodiment shown in FIG. 4, the holding plate 26 is flat and elongate and connects a central region of each end piece 18,20. Holding plate 26 supports a pyramid on each side and therefore, to obtain the therapeutic effects in accordance with the teachings of the invention, the polarized end pieces 18,20 must be dimensioned to provide a magnetic field to completely surround both pyramids P1,P2.

Figure 5:
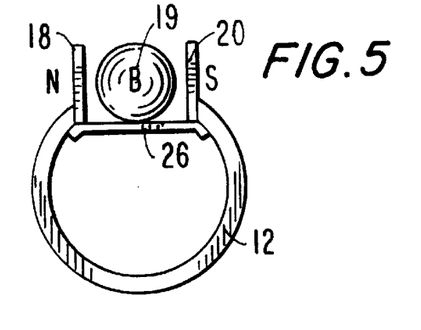
FIG. 5 is a schematic elevation view of a modification of the device of FIG. 1, with the pyramid being replaced by a sphere.

Instead of the interceptor means consisting of a pyramid, it is conceivable that the interceptor means comprise other physical shapes and configurations, i.e., perfect solids of revolution of selected dimensions. For example, in the embodiment shown in FIGS. 5 and 6, the interceptor means comprise a solid sphere 19 appropriately mounted to the holding plate 26 in a position between the polarized end pieces 18,20. The end pieces 18,20 must be constructed to provide or create a magnetic field therebetween such that the entire sphere is situated within the created magnetic field. The use of a sphere or other non-pyramidal structure makes it possible to create a variety of magnetic vortices having different shapes and characteristics, e.g., a pyramid in combination with a sphere. In addition, the pyramid P does not have to be a four-sided pyramid but may be, e.g., a three-sided pyramid or a cone.

In a similar manner as more than one musical note or combination of notes can be harmonious and have a soothing effect, more than one magnetic vortical shape may be formed, which have advantageous effects, and whose proportions differ from that of Cheops pyramid. Various proportions and materials of the interceptor means with various shapes can also be made to suit a particular body part. For example, as noted above, the embodiments of FIGS. 5 and 6 could be used as rings for the fingers.

Figures 6, 7A, 8:
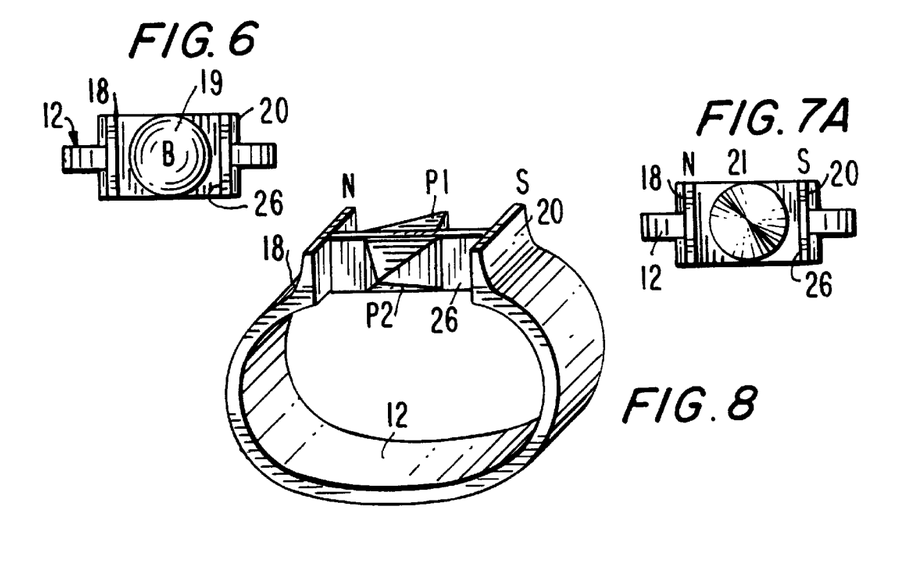
FIG. 6 is a schematic top plan view of the device shown in FIG. 5.
FIG. 7A is a schematic top plan view of the device shown in FIG. 7.
FIG. 8 is a perspective view of still another modification of the device according to the invention.

In addition, the embodiments shown in FIGS. 7, 7A and 8 can be used as rings. In the embodiment shown in FIGS. 7 and 7A, the magnet 12 constitutes the frame and is substantially circular and the interceptor means comprise a solid cone 21 appropriately mounted to a flat holding plate 26 in a position between the polarized end pieces 18,20. The end pieces 18,20 must be constructed to provide or create a magnetic field therebetween such that the entire cone 21 is situated within the created magnetic field. Also, it should be pointed out that an increase in the size of the magnetic field created between the end pieces 18,20 is facilitated by the fact that the size of the end pieces 18,20 is larger than the size of the magnet 12 (See FIG. 7A).

In the embodiment shown in FIG. 8, the holding plate 26 is attached to the end pieces so that it extends the two pyramids P1 and P2 in a direction transverse to the axial or longitudinal direction of the magnet 12 and is placed centrally between the edges of the polarized end pieces 18,20 of the magnet 12, which in this embodiment are part of the magnet 12. Two pyramids P1,P2 are mounted to the holding plate 26, one on each side, and the dimensions of the pyramids and the end pieces are selected so that the pyramids are entirely encompassed within the magnetic field generated between the end pieces 18,20 of the magnet 12.

With respect to the particular part of the body in connection with which the devices in accordance with the invention can be used, the embodiments shown in FIGS. 2A and 4 can be used as bracelets for the wrist or ankle, the embodiment shown in FIG. 9 can be used as a necklace or a collar, its four magnetic vortices would be placed, for example, one near the medulla at the back of the neck, two near the tonsils at each side of the neck and one near the heart or the thyroid. The structure of each pyramidal unit is the same, i.e., two end pieces 18,20 creating a magnetic field therebetween and an interceptor structure such as the pyramid situated between the end pieces and mounted on a holding plate or other mounting means which also attaches the end pieces together. The magnet portions between the end pieces 18,20 have a substantially circular cross-section and can be sized as desired.

Figure 10:
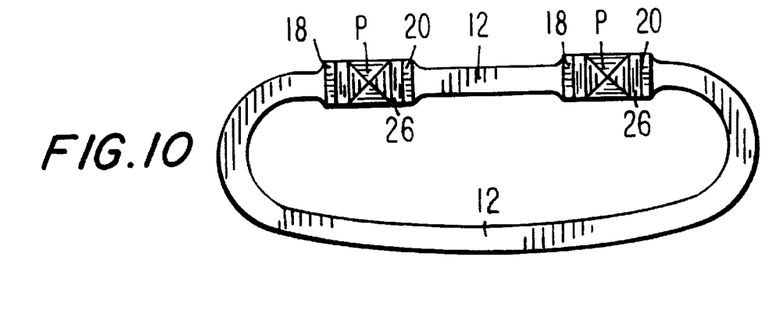
FIG. 10 is a plan view of still another embodiment of the magnetic vortex device according to the invention.
Figure 10A:
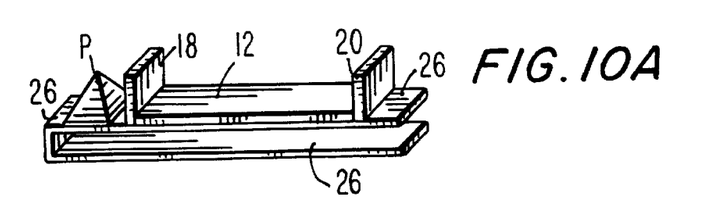
FIG. 10A is a sketch of an embodiment of this invention, illustrating a pyramid intercepting only one pole flux.
Figure 11:
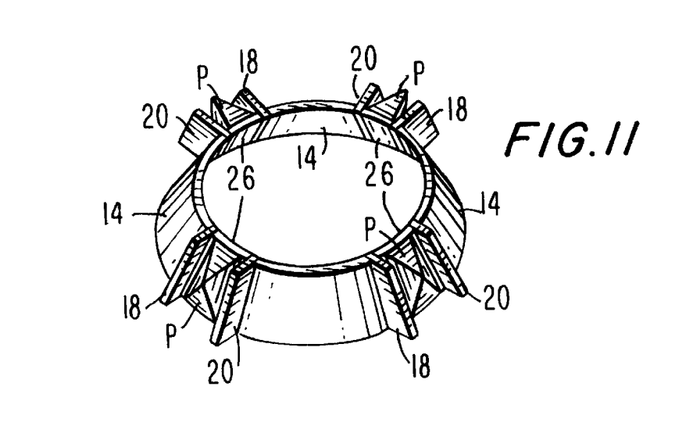
FIG. 11 is a schematic perspective view of a further embodiment of the magnetic vortex device according to the invention.

FIG. 11 shows a device in accordance with the invention which can be used as a bracelet for the arm above the elbow or above the knee or over the breast. In the event the bracelet of FIG. 11 cannot be worn, it could be replaced by a brooch or breast pin attached to the clothes. At least one of the mounting plates 26 supporting a respective one of the pyramids and connecting the associated two polarized end pieces can be made in the shape of a buckle and a catch to open and close the bracelet, collar or the pin shown in FIG. 10A. Further, it is entirely possible to provide different interceptor structures between different opposed end pieces, to thereby obtain varying magnetic vortex effects and associated therapeutic effects.

FIG. 10A shows a magnetic vortex device in accordance with the invention which can be worn as a pin. In this embodiment of the device 10, the mounting plate 26 is U-shaped, to thereby receive an article of clothing between the legs of the "U". The legs of the "U" are substantially flat and the polarized end pieces 18,20 and pyramid are mounted on one of the legs. In this embodiment, instead of the pyramid P being mounted between the end pieces 18,20, it is arranged proximate one of the end pieces 18 at side opposite the side in opposed relationship to the other end piece 20, i.e., thus not between the end pieces. Although, it may be considered preferable to place the pyramid between the polarized end pieces and thus directly in the magnetic field created between the end pieces, as shown in the embodiments described above, it is nevertheless possible to position the pyramid or other interceptor structure in the magnetic field created at one of the opposed end pieces because there is a strong magnetic field proximate each end piece.

In the event that it is desired to apply the vortical magnetic energy to the scalp of the head, a hairpin can be formed by two magnets 12 and two pyramids P as shown in FIG. 10, which can also be used as a breast pin. The construction of the mounting plates 26, pyramids P and end pieces 18,20 can be as disclosed in any of the embodiments above, or as set forth below.

Figure 12:
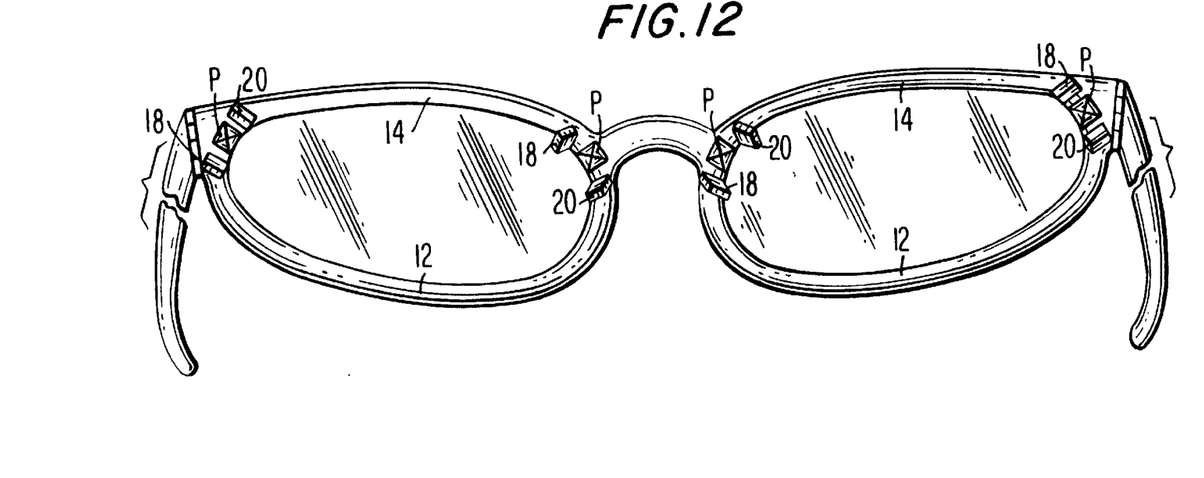
FIG. 12 is a sketch of another embodiment of the magnetic vortex device according to the invention.
Figure 12A:
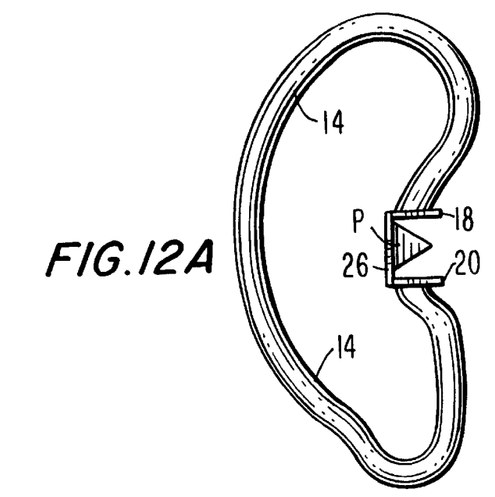
FIG. 12A is a sketch of another embodiment of the magnetic vortex device according to the invention.

When it is desirable to generate the magnetic vortex in accordance with the invention proximate the ear, the device may have the shape as shown in FIG. 12A, i.e., the magnet 12 has the shape or contour of a typical ear with two end pieces 18,20 defining a gap therebetween, the mounting plate 26 supporting the pyramid P between the end pieces 18,20.

To generate the magnetic vortical energy proximate the eyes or to the frontal sinus between the eyebrows, the device can take the form of spectacles or glasses as shown in FIG. 12, where the magnets 12 are carried by a plastic frame and the pyramids P are also seated on the frame. In this embodiment, there is no need for supporting plate 26.

Figure 13:
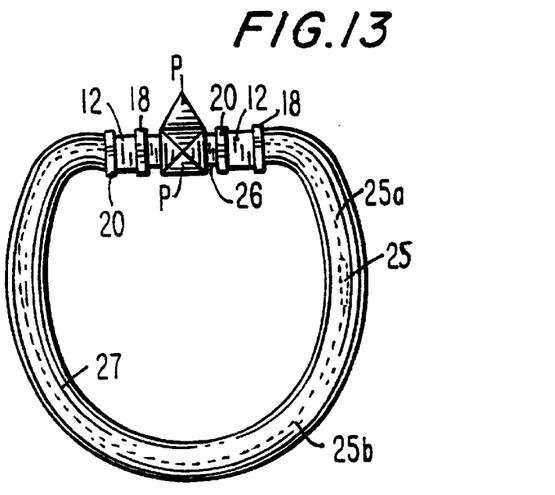
FIG. 13 is a sketch showing an embodiment according to the invention illustrating two different magnets connected together by a magnetic material so as to form a closed magnetic path.

FIG. 13 shows an embodiment where two magnetizable members 12 are used to magnetize the end pieces 18,20 which are situated in opposed relationship to each other but completely separated from one another. To enable the magnetic field to run through the device, which in this case has the form of a ring, a magnetic or magnetizable material 27 is provided in the ring to connect the two external pole pieces not facing the pyramid so as to form a closed magnetic path. Advantages of this embodiment are that only a small portion of the ring is a magnet, i.e., that portion which provides the magnetic properties to the end pieces 18,20. The remaining portion of the ring is not a magnet but is only magnetizable so that magnetic lines of force of flux lines pass therethrough. Alternatively, the magnets 12 may be magnetized by an electromagnet system shown in dotted lines. This system would include electricity storage means 25 and electrical leads 25a,25b leading to the magnets 12. It should be understood that any of the permanent magnets shown in the other embodiments can of course be substituted for by an electromagnetic system.

Naturally, when the device is intended to be worn by human beings, the magnet 12 is covered by silver, gold or filigree or other covering material, to render it more attractive.

Having described specific preferred embodiments of the invention with reference to the accompanying drawings, it is to be understood that the invention is not limited to those precise embodiments and that various changes and modifications may be effected therein by one skilled in the art without departing from the scope or spirit of the invention as defined in the appended claims. For example, it should be noted that the present invention is not limited to the use of calcium carbonate and granite as in the Cheops pyramid. It may be desirable to replace the material of the pyramid by a precious stone, semiprecious stone or natural stones. All crystals could be used such as quartz, emerald, or sapphire, whether natural or synthetic. It may also be desirable to have a blanket, or a smaller pad, containing a plurality of magnetic vortex devices to cover all of the body of only a part thereof. A mattress, a beret or a vest may be tailored to include many magnetic vortex devices.

I claim:

1. A magnetic vortex device for generating a magnetic vortex to be applied to the human body in order to treat ailments or diseases, comprising:

a frame, magnetic field generating means arranged in connection with said frame for generating a magnetic field, said generating means comprising at least one magnetized or magnetizable member arranged to have first and second opposed portions separated from one another to define a space therebetween, said first and second portions being polarized or polarizeable such that said first portion has an opposite polarity than said second portion whereby magnetic flux lines extend between said first and second portions to generate the magnetic field, interceptor means for intercepting at least a portion of the magnetic flux lines extending between said first and second portions and preventing that portion of the magnetic flux lines from passing in a direct line between said first and second portions, and support means for supporting said interceptor means in a position between said first and second portions.

2. The magnetic vortex device of claim 1, wherein said at least one member comprises a single C-shaped member constituting a permanent magnet, said frame being constituted by said C-shaped member.

3. The magnetic vortex device of claim 1, wherein said at least one member comprises a single C-shaped member constituting a flexible magnet, said frame being constituted by said C-shaped member.

4. The magnetic vortex device of claim 1, wherein said generating means comprise an electromagnet coupled to said first and second portions of said at least one member.

5. The magnetic vortex device of claim 1, wherein said support means comprise a flat, dia-magnetic elongate plate connected at a first end to said first portion of said at least one member and at a second end to said second portion of said at least one member.

6. The magnetic vortex device of claim 5, wherein said interceptor means comprise a plurality of pyramids, said plate being structured and arranged to support on a single face said plurality of pyramids.

7. The magnetic vortex device of claim 1, wherein said at least one member comprises first and second members mounted on said frame, said first member encompassing said first opposed portion of said at least one member and said second member encompassing said second opposed portion of said at least one member, said first and second member being magnetically coupled through said frame.

8. The magnetic vortex device of claim 1, wherein said interceptor means comprise a solid pyramid of dia-magnetic material.

9. The magnetic vortex device of claim 1, wherein said interceptor means comprise a plurality of pyramids, said support means being structured and arranged to support each of said pyramids.

10. The magnetic vortex device of claim 1, wherein said support means comprise a flat plate connected at a first end to a middle region of said first portion of said at least one member and at a second end to a middle region of said second portion of said at least one member, said interceptor means comprising a pair of pyramids symmetrically seated on each side of said plate.

11. The magnetic vortex device of claim 1, wherein said interceptor means comprise a three-dimensional structure consisting of natural ore.

12. The magnetic vortex device of claim 1, wherein said interceptor means comprise a three-dimensional structure consisting of vegetable materials.

13. The magnetic vortex device of claim 1, wherein said interceptor means comprise a three-dimensional structure consisting of synthetic material.

14. The magnetic vortex device of claim 1, wherein said frame comprises a plurality of separated elongate frame sections and said interceptor means comprise a plurality of pyramids, said support means comprising a plate section for connecting each set of opposed ends of adjacent frame sections, said at least one member comprising a plurality of members, one arranged at both ends of each of said frame sections, at least one of said pyramids being supported on each of said plate sections.

15. The magnetic vortex device of claim 14, wherein said first and second portions which the magnet means is made up of comprises a plurality of flexible permanent magnets, placed magnetically in series such that the magnetic field extending from the respective poles of said plurality of flexible permanent magnets form a closed magnetic circuit of unidirectional flow.

16. The magnetic vortex device of claim 1, wherein said interceptor means comprise precious or semiprecious gemstones or natural stones having the shape of perfect solids of revolution.

17. The magnetic vortex device of claim 1, wherein said interceptor means comprise a four-sided pyramid having a height to width ratio of about 7:11, said first and second portions of said at least one member being flat and longitudinally displaced from one another, said pyramid being positioned on said support means such that respective sides of said pyramid are parallel, in opposed relationship and substantially equal in width and height to said flat portions of said at least one member.

18. The magnetic vortex device of claim 1, wherein said frame is substantially circular and said end portions have a larger size than a cross-sectional size of said frame, said interceptor means comprising a solid sphere.

19. A magnetic vortex device for generating a magnetic vortex to be applied to the human body in order to treat ailments or diseases, comprising:
   a U-shaped frame having a pair of legs adapted to receive an article of clothing,
   magnetic field generating means arranged on one of said legs for generating a magnetic field, said generating means comprising first and second magnetized or magnetizable members separated from one another and polarized or polarizeable such that said first member has an opposite polarity than said second member, said first member having first and second sides whereby said first side is in opposed relationship to said second member, and
   interceptor means for intercepting magnetic flux lines formed in connection with said first member, said interceptor means being arranged proximate said first member on said second side of said first member to intercept magnetic flux lines associated with said first member.

20. A magnetic vortex ring for generating a magnetic vortex to be applied to a human finger in order to provide therapeutic effects, comprising:
   a substantially circular frame made of a magnetizable material,
   magnetic field generating means arranged on said frame for generating a magnetic field, said generating means comprising first and second magnetized or magnetizable members separated from one another to define a space therebetween, said first and second members being polarized or polarizeable such that said first member has an opposite polarity than said second member and magnetic flux lines extend between said first and second member to generate the magnetic field,
   interceptor means for intercepting at least a portion of the magnetic flux lines extending between said first and second members and preventing that portion of the magnetic flux lines from passing in a direct line between said first and second members,
   support means for supporting said interceptor means in a position between said first and second members, and
   cover means for covering a section of said frame between said first and second members in which said interceptor means are not situated.

* * * * *